(12) United States Patent
Brocchini et al.

(10) Patent No.: US 7,939,630 B2
(45) Date of Patent: *May 10, 2011

(54) CONJUGATED BIOLOGICAL MOLECULES AND THEIR PREPARATION

(75) Inventors: Stephen James Brocchini, Welwyn Garden City (GB); Antony Robert Godwin, Bristol (GB); Elisa Pedone, Leytonstone (GB); Ji-Won Choi, Leytonstone (GB); Sunil Shaunak, Hertfordshire (GB)

(73) Assignee: Polytherics Limited, Longon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/458,931

(22) Filed: Jul. 28, 2009

(65) Prior Publication Data

US 2009/0298154 A1 Dec. 3, 2009

Related U.S. Application Data

(63) Continuation of application No. 10/564,340, filed as application No. PCT/GB2004/002994 on Jan. 11, 2006, now Pat. No. 7,595,292.

(30) Foreign Application Priority Data

Jul. 11, 2003 (GB) .................................. 0316294.8

(51) Int. Cl.
*C07K 1/13* (2006.01)
(52) U.S. Cl. ...................................................... 530/345
(58) Field of Classification Search .................. None
See application file for complete search history.

(56) References Cited

U.S. PATENT DOCUMENTS

| | | | |
|---|---|---|---|
| 5,786,387 A | 7/1998 | Watanabe et al. | |
| 6,153,655 A | 11/2000 | Martinez et al. | |
| 6,395,266 B1 | 5/2002 | Martinez et al. | |
| 6,638,500 B1 | 10/2003 | El-Tayar et al. | |
| 6,803,438 B1 | 10/2004 | Brocchini et al. | |
| 6,828,412 B1 | 12/2004 | Brocchini et al. | |
| 7,005,454 B2 | 2/2006 | Brocchini et al. | |
| 7,101,840 B2 | 9/2006 | Brocchini et al. | |
| 2001/0011115 A1 | 8/2001 | Harris et al. | |
| 2002/0019446 A1 | 2/2002 | Brocchini et al. | |
| 2002/0037949 A1 | 3/2002 | Harris et al. | |
| 2002/0040076 A1 | 4/2002 | Harris et al. | |
| 2002/0052430 A1 | 5/2002 | Harris et al. | |
| 2002/0103259 A1 | 8/2002 | Martinez et al. | |
| 2003/0068384 A1 | 4/2003 | Brocchini et al. | |
| 2004/0043002 A1 | 3/2004 | El-Tayar et al. | |
| 2004/0059025 A1 | 3/2004 | Harris et al. | |

FOREIGN PATENT DOCUMENTS

| | | |
|---|---|---|
| WO | 95/34326 | 12/1995 |
| WO | 99/45964 | 9/1999 |
| WO | 99/55377 | 11/1999 |
| WO | 01/17515 | 3/2001 |
| WO | 01/18080 | 3/2001 |
| WO | 01/05818 | 7/2001 |

OTHER PUBLICATIONS

Declaration of Andrew George under 37 C.F.R. § 1.132 filed on Mar. 24, 2009 in parent U.S. Appl. No. 10/564,340.*
Brocchini et al. "Molecular yardsticks. Synthesis of extended equilibrium transfer alkylating cross-link reagents and their use in the formation of macrocycles" *J. Am. Chem. Soc.* 110:5211-5212 (1988).
Brocchini et al. "Disulfide bridge based PEGylation of proteins" *Adv. Drug Deliv. Rev.* 60:3-12 (Jan. 2008).
del Rosario et al. "Sulfhydryl site-specific cross-linking and labeling of monoclonal antibodies by a fluorescent equilibrium transfer alkylation cross-link reagent" *Bioconjugate Chem.* 1:51-59 (1990).
Kenkel *Analytical Chemistry for Technicians Third Ed.*, CRC Press, p. 472 (2002).
Liberatore et al. "Site-directed chemical modification and cross-linking of a monoclonal antibody using equilibrium transfer alkylating cross-link reagents" *Bioconjugate Chem.* 1:36-50 (1990).
Oae & Okuyama (eds.) *Organic Sulfur Chemistry: Biochemical Aspects*, CRC Press, p. 147 (1992).
Roberts et al. "Chemistry for peptide and protein PEGylation" *Adv. Drug Deliv. Rev.* 54:459-476 (2002).
Shaunak et al. "Site-specific PEGylation of native disulfide bonds in therapeutic proteins" *Nature Chem. Biol.* 2:312-313 (2006).
Smy "When cash is no objective" *Hospital Doctor* 4:29 (Jul. 2006).
Wilbur et al. "Monoclonal antibody Fab' fragment cross-linking using equilibrium transfer alkylation reagents. A strategy for site-specific conjugation of diagnostic and therapeutic agents with F(ab')$_2$ fragments" *Bioconjugate Chem.* 5:220-235 (1994).
Kornfield et al. "The synthesis of furan, thiophene, and pyrrole-3,4-dicarboxylic esters" *J. Org. Chem.* 19:1671-1680 (1954).
International Search Report for PCT/GB2004/002994, four pages, mailed Jan. 31, 2005.

(Continued)

*Primary Examiner* — Christina Bradley
(74) *Attorney, Agent, or Firm* — Nixon & Vanderhye P.C.

(57) ABSTRACT

Novel biologically active compounds of the general formula (I) in which one of X and X' represents a polymer, and the other represents a hydrogen atom; each Q independently represents a linking group; W represents an electron-withdrawing moiety or a moiety preparable by reduction of an electron-withdrawing moiety; or, if X' represents a polymer, X-Q-W— together may represent an electron withdrawing group; and in addition, if X represents a polymer, X' and electron withdrawing group W together with the interjacent atoms may form a ring; each of $Z_1$ and $Z_2$ independently represents a group derived from a biological molecule, each of which is linked to A and B via a nucleophilic moiety; or $Z_1$ and $Z_2$ together represent a single group derived from a biological molecule which is linked to A and B via two nucleophilic moieties; A is a $C_{1-5}$ alkylene or alkenylene chain; and B is a bond or a $C_{1-4}$ alkylene or alkenylene chain; are formed by conjugating a suitable polymer to a suitable biologically active molecule via nucleophilic groups in said molecule, preferably via a disulphide bridge.

16 Claims, 5 Drawing Sheets

OTHER PUBLICATIONS

Int'l Preliminary Report on Patentability for PCT/GB2004/002994, ten pages, mailed Jan. 16, 2006.

Bayer Healthcare and Bayer Schering Pharma's Opposition to European Patent 1648518, 21 pages, and its English translation, dated Jun. 5, 2010.

Brocchini "Molecular yardsticks" Ph.D. dissertation thesis at University of Michigan, pp. 1-286 (1990).

Chow et al. "Gastric H+-K+—ATPase activity is inhibited by reduction of disulfide bonds in β-subunit" Am. J. Physiol. 263:C39-C46 (1992).

Del Rosario et al. "Streptavidin-biotinylated IgG conjugates: A simple procedure for reducing polymer formation" Nucl. Med. Biol. 19:417-421 (1992).

Dennis et al. "Selection and characterization of a new class of peptide exosite inhibitors of coagulation factor Vlla" Biochemistry 40:9513-9521 (2001).

Zloh et al. "The effect of hydrogen bonding interactions on the reactivity of a novel disulfied-specific PEGylation reagent" *Physical Chemistry 2006 Proceedings*, F-3-O, pp. 347-349 (Sep. 2006).

* cited by examiner

—○— NIBSC(UK) Interferon-α 2b standard:- $ED_{50}$ = 38 pg/ml

--●-- Our native Interferon-α 2b:- $ED_{50}$ = 90 pg/ml

\* 3-5 pg/ml is equivalent to 1 IU/ml.

• Our native Interferon-α 2b:-  ED$_{50}$ = 90 pg/ml

□ Our chemically treated but unpegylated native Interferon-α 2b:-  ED$_{50}$ = 40 pg/ml

CONJUGATED BIOLOGICAL MOLECULES AND THEIR PREPARATION

CROSS-REFERENCE TO RELATED APPLICATIONS

This application is a Continuation of application Ser. No. 10/564,340, filed Jan. 11, 2006 now U.S. Pat. No. 7,595,292; which is a U.S. national stage under 35 U.S.C. 371 of Intl Application No. PCT/GB2004/002994, filed Jan. 11, 2006; the contents of which are incorporated by reference herein.

FIELD OF THE INVENTION

This invention relates to conjugated biological molecules and their preparation from novel chemically functionalised derivatives of polymers such as polyethylene glycol.

BACKGROUND OF THE INVENTION

Many therapeutically active molecules do not possess the properties required to achieve efficacy in clinical medical use. For example, therapeutically active proteins and poly-peptides are now being discovered and produced by the biopharmaceutical industry and by genetic engineering. Although there are currently at least 80 protein based medicines marketed in the United States with at least 350 more protein based medicines undergoing clinical trails (Harris J, Chess R: Effect of Pegylation on pharmaceuticals. Nature Review Drug Discovery, 2003, 2, 214-221), most native proteins do not make good medicines because upon administration to patients there are several inherent drawbacks that include: (1) proteins are digested by many endo- and exopeptidases present in blood or tissue, (2) many proteins are immunogenic to some extent and (3) proteins can be rapidly excreted by kidney ultrafiltration. Other molecules used as active therapeutic agents in medicines that are systemically toxic or lack optimal bioavailability and pharmacokinetics include low molecular weight molecules where an effective dose is limited by toxicity. Such molecules are routinely used to treat inflammation and conditions due to malignancies, infection and autoimmune disease.

SUMMARY OF THE INVENTION

Water soluble, synthetic polymers, particularly polyalkylene glycols, are used to conjugate therapeutically active molecules such as proteins. These therapeutic conjugates have been shown to favourably alter pharmacokinetics by prolonging circulation time and decreasing clearance rates, decrease systemic toxicity, and in several cases, to display increased clinical efficacy. This process of covalently conjugating polyethylene glycol, PEG, to proteins is commonly known as "PEGylation" however many different polymers have been examined as conjugating polymers.

Many polymer reagents for conjugation comprise conjugating chemical functionality that is hydrolytically unstable. Examples of hydrolytically unstable polymeric conjugating reagents are active esters that include, for example, polyalkylene oxide-N-succinimide carbonates (Zalipsky U.S. Pat. No. 5,122,614). These reagents have relatively short half lives in aqueous media, that includes blood or plasma. This results in the need to add large stoichiometric excesses of the conjugating polymer reagent. The hydrolytic stability of the reagent is important because the requirement to add stoichiometric excesses for protein conjugation requires significant effort and cost to purify the polymer-protein conjugate from the reaction mixture. Furthermore, these hydrolytically unstable reagents tend to undergo preferentially, reaction with amine chemical functionality in the protein, particularly to the $\epsilon$-amine of lysine residues. Since most proteins of interest have more than one lysine residue, and frequently many lysine residues, then conjugation tends to be non-specific in that it occurs at many residue sites on the protein. It is possible to purify the conjugating reaction mixture to isolate proteins conjugated to one polymer molecule, however it is not possible, to isolate at a reasonable cost, polymer-protein conjugates that are all conjugated to the same amine group on the protein. Non-specific conjugation frequently results in impaired protein function. For example antibodies and antibody fragments with random poly(alkylene oxide) attachment via lysine residues result in modified antibodies (or modified antibody fragments) able to bind target antigen with reduced affinity, avidity or specificity. Additionally, amine specific polymer conjugating reagents require conjugating reaction conditions that must be selected to ensure that the amines on the protein are not protonated. These conditions require moderately high pH media (8-10), this allows the amine moieties to be reactive enough for reaction with the polymer conjugating reagent. High pH conditions are frequently deleterious to the protein causing structural changes and denaturation. These processes result in impairment of protein function. Amine specific polymer conjugation reagents tend to bind to accessible amine sites on the protein. These reagents can be termed kinetic reagents. They are labile and undergo a reaction with the most assessable amino nucleophilic sites on the protein. Amine specific polymer conjugating reagents that conjugate by amine acylation result in the loss of positive charge on the amine group of the amino acid residue on the protein that would normally be present under physiological conditions for the unconjugated protein. These features of amine specific polymer conjugating reagents often leads to partial impairment of the function of the protein. Other conjugating functional groups incorporated in polymers for conjugation to protein and that are amine specific and frequently hydrolytically labile include isocyanate (WO 94/04193) and carbonates (WO 90/13540).

Particularly relevant for optimised efficacy and to ensure dose to dose consistency is to make certain that the number of conjugated polymer molecules per protein is the same and that each polymer molecule is specifically covalently conjugated to the same amino acid residue in each protein molecule. Non-specific conjugation at sites along a protein molecule results in a distribution of conjugation products and frequently, unconjugated protein, to give a complex mixture that is difficult, tedious, and expensive to purify.

Thiol specific polymer conjugating reagents for proteins have been developed to address the limitations for the propensity of the conjugating reagent to undergo hydrolysis that is competitive with conjugation to the protein, non-specific polymer conjugation at different amino acid residues in the protein, and the need for high pH conjugating reaction conditions. Thiol specific polymer conjugating reagents can be utilised at pH values close to neutrality where the amine functional moieties on the amino acid residues of the protein are protonated and thus cannot effectively compete in the conjugation reaction with the polymer conjugating reagent. Thiol specific polymer conjugating reagents that are relatively more hydrolytically stable than are the aforementioned amine specific reagents can be utilised at a lower stoichiometric excess thus reducing the cost during purification of the polymer-protein conjugate. Conjugating functional moieties that are broadly selective for thiol groups include iodoacetamide, maleiimide (WO 92/16221), vinylsulfone (WO 95/13312 and WO 95/34326), vinyl pyridines (WO 88/05433), and acrylate and methacrylate esters (WO 99/01469). These thiol selective conjugating moieties yield a single thioether conjugating bond between the polymer.

Most proteins do not have free sulfhydrals because these sulfhydrals undergo rearrangement and scrambling reactions with the disulfide bridges within the protein resulting in impaired protein function. For proteins that do have free sulfhydrals, these sulfhydrals are frequently critical for protein function. Typically in a protein, the number of sulfhydral moieties is less than the number of amine moieties (e.g. lysine or histadine). Since conjugation to a protein can be made to be specific at thiol groups and since proteins do not typically have free thiol groups, there are examples of site-specific modification of protein by mutagenesis to introduce thiol sites for PEG attachment. However such modifications increase costs significantly. The introduced free sulhydral can have the similar limitations as mentioned heretofore in the engineered protein for protein scrambling and protein dimerisation. Also the process of mutagensis and production of the modified protein from bacterial sources frequently causes the free sulfhydral to be bound in a disulfide bond with glutathione, for example. Interleukin-2, for example, has been modified by mutagenesis to replace a threonine residue by a cysteine to allow site specific attachment of PEG. [Goodson R J, Katre N V; Bio/Technology (1990) 8, 343-346].

It is known in the art that conjugating parameters have to be optimally matched with the therapeutically active molecule of interest in terms of polymer morphology, molecular weight characteristics, chemical functionality. Although the polymer protein conjugate, can display many favourable and necessary properties needed for safe, effective medical use, the effect of polymer conjugation on the activity and stability of the protein is of vital importance for performance. Conjugation variables related to the location and amount of conjugation and polymer characteristics must be optimally correlated with biological and physicochemical properties.

We have now found a series of novel reagents which can be used inter alia to conjugate with both sulphur atoms derived from two cysteine residues in a protein to give novel thioether conjugates. The invention in the first instance is intended for the conjugation of the two sulphur atoms that form natural disulphide bridges in native proteins. Disulphide bonds are found in medically relevant proteins, specifically, secretory proteins, lysosomal proteins, and the exoplasmic domains of membrane proteins. The technology provides clear advantages over known techniques for conjugating polymers to proteins.

DETAILED DESCRIPTION OF SPECIFIC EMBODIMENTS

Figure 1:
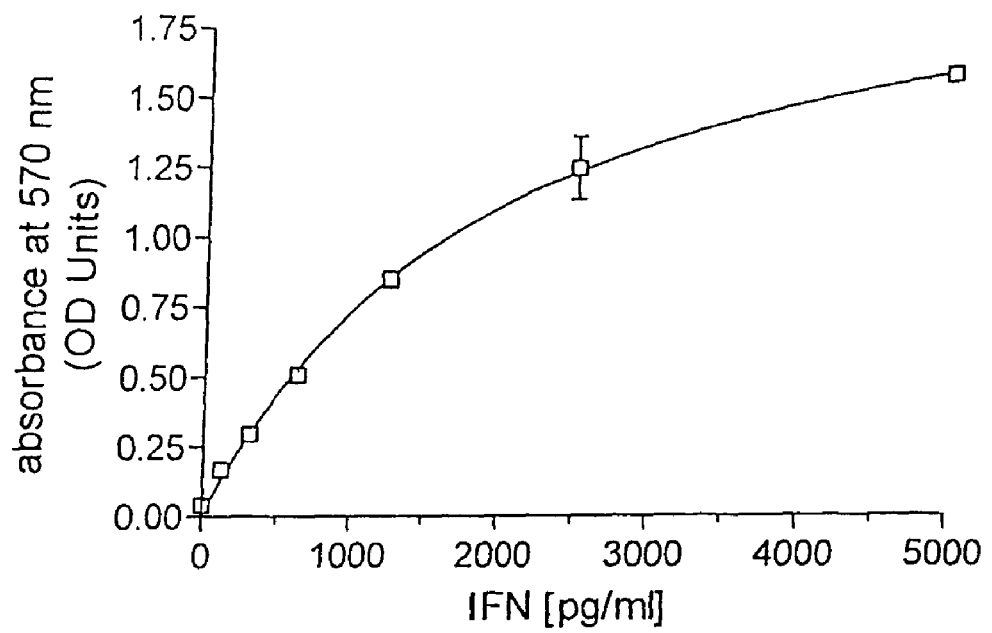
FIG. 1 shows the standard curve obtained for different forms of polymer-conjugated interferon obtained in Example 7.

The present invention provides a compound of the general formula.

in which one of X and X' represents a polymer, and the other represents a hydrogen atom;

each Q independently represents a linking group;

W represents an electron-withdrawing moiety or a moiety preparable by reduction of an electron-withdrawing moiety; or, if X' represents a polymer, X-Q-W— together may represent an electron withdrawing group; and in addition, if X represents a polymer, X' and electron withdrawing group W together with the interjacent atoms may form a ring;

each of $Z^1$ and $Z^2$ independently represents a group derived from a biological molecule, each of which is linked to A and B via a nucleophilic moiety; or $Z^1$ and $Z^2$ together represent a single group derived from a biological molecule which is linked to A and B via two nucleophilic moieties;

A is a $C_{1-5}$ alkylene or alkenylene chain; and

B is a bond or a $C_{1-4}$ alkylene or alkenylene chain.

A polymer X or X' may for example be a polyalkylene glycol, a polyvinylpyrrolidone, a polyacrylate, for example polyacryloyl morpholine, a polyoxazoline, a polyvinylalcohol, a polyacrylamide or polymethacrylamide, for example polycarboxymethacrylamide, or a HPMA copolymer. Additionally X or X' may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer X or X' may be a homopolymer, random copolymer or a structurally defined copolymer such as a block copolymer. For example X or X' may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride. Naturally occurring polymers may also be used, for example polysaccharides such as chitin, dextran, dextrin, chitosan, starch, cellulose, glycogen, poly(sialylic adic) and derivatives thereof. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted polyalkylene glycols, for example methoxypolyethylene glycol, may be used. In a preferred embodiment of the invention, a single-chain polyethylene glycol is initiated by a suitable group, for example an alkoxy, e.g. methoxy, aryloxy, carboxy or hydroxyl group, and is connected at the other end of the chain to the linker group Q.

The polymer X or X' may optionally be derivatised or functionalised in any desired way. For example, polymers with two or more chemical moieties for conjugation that are the subject of this invention may be used to create conjugates of two or more linked bioactive molecules. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. Multimeric conjugates that contain more than one biological molecule, typically a biologically active polypeptide or drug can result in synergistic and additive benefits. If desired, the polymer may be coupled to a solid support using conventional methods.

The optimum molecular weight of the polymer will of course depend upon the intended application. Preferably, the number average molecular weight is in the range of from 500 g/mole to around 75,000 g/mole. When the compound of the general formula I is intended to leave the circulation and penetrate tissue, for example for use in the treatment of inflammation caused by malignancy, infection or autoimmune disease, or by trauma, it may be advantageous to use a lower molecular weight polymer in the range 2000-30,000 g/mole. For applications where the compound of the general formula I is intended to remain in circulation it may be advantageous to use a higher molecular weight polymer, for example in the range of 20,000-75,000 g/mole.

The polymer to be used should be selected so the conjugate is soluble in the solvent medium for its intended use. For biological applications, particularly for diagnostic applications and therapeutic applications for clinical therapeutical administration to a mammal, the conjugate will be soluble in aqueous media. Many proteins such as enzymes have utility in industry, for example to catalyze chemical reactions. For conjugates intended for use in such applications, it may be necessary that the conjugate be soluble in either or both aqueous and organic media. The polymer should not impair the intended function of the biological molecule(s).

A linking group Q may for example be a direct bond, an alkylene group (preferably a $C_{1-10}$ alkylene group), or an optionally-substituted aryl or heteroaryl group, any of which may be terminated or interrupted by one or more oxygen atoms, sulphur atoms, —NR groups (in which R has the meaning given below), keto groups, —O—CO— groups and/or —CO—O— groups. Suitable aryl groups include phenyl and naphthyl groups, while suitable heteroaryl groups include pyridine, pyrrole, furan, pyran, imidazole, pyrazole, oxazole, pyridazine, primidine and purine. The linkage to the polymer may be by way of a hydrolytically labile bond, or by a non-labile bond.

Substituents which may be present on an optionally substituted aryl or heteroaryl group include for example one or more of the same or different substituents selected from —CN, —$NO_2$, —$CO_2R$, —COH, —$CH_2OHR$, —COR, —OR, —OCOR, —$OCO_2R$, —SR, —SOR, —$SO_2R$, —NHCOR, —NRCOR, —$NHCO_2R$, —$NR'CO_2R$, —NO, —NHOH, —NR'OH, —C=N—NHCOR, —C=N—NR'COR, —$N+R_3$, —$N^+HR_3$, —$N^+HR_2$, —$N^+H_2R$, halogen, for example fluorine or chlorine, —C≡CR, —C≡$CR_2$ and —C=CHR, in which each R or R' independently represents a hydrogen atom or an alkyl (preferably $C_{1-6}$ alkyl) or an aryl (preferably phenyl) group. The presence of electron withdrawing substituents is especially preferred.

W may for example represent a keto or aldehyde group CO, an ester group —O—CO— or a sulphone group —$SO_2$—, or a group obtained by reduction of such a group, e.g. a CH.OH group, an ether group CH.OR, an ester group CH.O.C(O)R, an amine group $CH.NH_2$, CH.NHR or $CH.NR_2$, or an amide CH.NHC(O)R or $CH.N(C(O)R)_2$. If X-Q-W— together represent an electron withdrawing group, this group may for example be a cyano group.

In the following portion of this specification, $Z^1$ and $Z^2$ will be referred to collectively as Z. It is a preferred embodiment of the invention that $Z^1$ and $Z^2$ together should represent a single biological molecule:

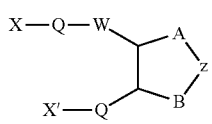

Z may be derived from any desired biological molecule, for example a protein. The protein may for example be a polypeptide, antibody, antibody fragment, enzyme, cytokine, chemokine or receptor. Constrained or cyclic polypeptides, which are usually cyclised through a disulphide bridge, and epitopes, may also be used. Specific examples of suitable biological molecules are listed below.

Preferably a nucleophilic moiety linking A or B to the group(s) Z is derived from a thiol group or amine group. Two thiol groups may be generated by partial reduction of a natural or engineered disulphide (cysteine) bridge. Amine groups may for example be lysine residues. Where $Z^1$ and $Z^2$ together form a single biological molecule which is linked to the groups A and B via two thiol groups, the compound of the formula I has the formula

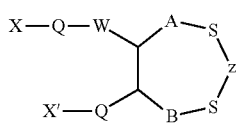

The invention also provides a process for the preparation of a compound of the general formula I, which comprises reacting either (i) a compound of the general formula

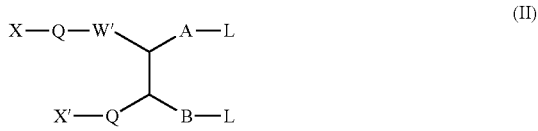

(II)

in which one of X and X' represents a polymer and the other represents a hydrogen atom;

Q represents a linking group;

W' represents an electron-withdrawing group, for example a keto group, an ester group —O—CO— or a sulphone group —$SO_2$—; or, if X' represents a polymer, X-Q-W' together may represent an electron withdrawing group;

A represents a $C_{1-5}$ alkylene or alkenylene chain;

B represents a bond or a $C_{1-4}$ alkylene or alkenylene chain; and each L independently represents a leaving group; or (ii) a compound of the general formula

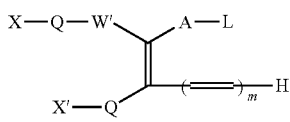

(III)

in which X, X', Q, W', A and L have the meanings given for the general formula II, and in addition if X represents a polymer, X' and electron-withdrawing group W' together with the interjacent atoms may form a ring, and m represents an integer 1 to 4; with a compound of the general formula $$Z(Nu)_2 \qquad (IV)$$

in which Z has the meaning given above and each Nu independently represents a nucleophilic group, for example a thiol or an amine group. If $Z^1$ and $Z^2$ are separate molecules, the reaction takes place in two successive steps with successive molecules $Z^1Nu$ and $Z^2Nu$.

The or each leaving group L may for example represent —SR, —SO$_2$R, —OSO$_2$R, —N$^+$R$_3$, —N$^+$HR$_2$, —N$^+$H$_2$R, halogen, or —OØ, in which R has the meaning given above, and Ø represents a substituted aryl, especially phenyl, group, containing at least one electron withdrawing substituent, for example —CN, —NO$_2$, —CO$_2$R, —COH, —CH$_2$OH, —COR, —OR, —OCOR, —OCO$_2$R, —SR, —SOR, —SO$_2$R, —NHCOR, —NRCOR, —NHCO$_2$R, —NR'CO$_2$R, —NO, —NHOH, —NR'OH, —C=N—NH-COR, —C=N—NR'COR, —N$^+$R$_3$, —N$^+$HR$_2$, —N$^+$H$_2$R, halogen, especially chlorine or, especially, fluorine, —C≡CR, —C≡CR$_2$ and —C=CHR, in which R and R' have the meanings given above.

Typical structures in which W' and X' together form a ring include

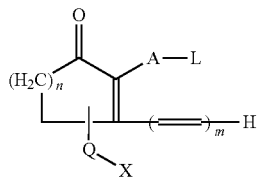

(IIIa)

in which n is an integer from 1 to 4, and

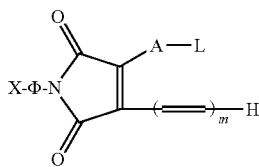

(IIIb)

A compound of the general formula (IV) in which each Nu is a thiol group may be prepared by partial reduction of a protein contain a cysteine link, i.e.

(V)

Suitably, the process according to the invention is carried out by partially reducing a disulfide bond derived from two cysteine amino acids in the protein in situ following which the reduced product reacts with the compound of formula (II) or (III). Disulfides can be reduced, for example, with dithiothreitiol, mercaptoethanol, or tris-carboxyethylphosphine using conventional methods. The process may be carried out in a solvent or solvent mixture in which all reactants are soluble. The biological molecule containing nucleophilic groups (e.g. protein) may be allowed to react directly with the compound of the general formula II or III in an aqueous reaction medium. This reaction medium may also be buffered, depending on the pH requirements of the nucleophile. The optimum pH for the reaction is generally between about 5.5 and about 8, for example about 7.4, preferably about 6.0-6.5. Reaction temperatures between 3-37° C. are generally suitable: proteins and other biological molecules may decompose or denature impairing function if the conjugation reaction is conducted at a temperature where these processes may occur. Reactions conducted in organic media (for example THF, ethyl acetate, acetone) are typically conducted at temperatures up to ambient, for example temperatures below 0° C.

A protein can contain one or a multiplicity of disulfide bridges. Reduction to give free sulfhyral moieties can be conducted to reduce one or a multiplicity of disulfide bridges in a protein. Depending on the extent of disulfide reduction and the stoichiometry of the polymeric conjugation reagent that is used, it is possible to conjugate one or a multiplicity of polymer molecules to the protein. Immobilised reducing agents may be used if it is desired to reduce less than the total number of disulfides, as can partial reduction using different reaction conditions or the addition of denaturants.

Alternatively the source of the thiol groups can be from cysteines or thiols not originally derived from a disulfide bridge. If the source of the thiol groups is a disulfide bridge, this may be intrachanin or interchain.

The biological molecule can be effectively conjugated with the reagents of the present invention using a stoichiometric equivalent or a slight excess of reagent, unlike many prior art reagents. However, since the reagents of the present invention do not undergo competitive reactions with aqueous media used to solvate proteins, it is possible to conduct the conjugation reaction with an excess stoichiometry of reagent. The excess reagent can be easily removed by ion exchange chromatography during routine purification of proteins.

The compounds of formulae (II) and (III) are novel, and accordingly the invention further provides these compounds per se. These novel reagents provide a breakthrough in conjugate technology, the chemical functional moiety on the polymer comprising a cross-functionalised, latently cross-conjugated, bis-alkylating moiety that is selective for two nucleophiles, particularly two thiols derived from a natural disulfide bond in proteins.

The immediate product of the process according to the invention is a compound of the general formula I in which W is an electron-withdrawing group. Such compounds have utility in themselves; because the process of the invention is reversible under suitable conditions, additionally compounds of formula (I) in which W is an electron-withdrawing moiety have utility in applications where release of the free protein is required, for example in direct clinical applications. An electron-withdrawing moiety W may, however, be reduced to give a moiety which prevents release of the protein, and such compounds will also have utility in many clinical, industrial and diagnostic applications.

Thus, for example, a moiety W containing a keto group may be reduced to a moiety W containing a CH(OH) group;

an ether group CH.OR may be obtained by the reaction of a hydroxy group with an etherifying agent; an ester group CH.O.C(O)R may be obtained by the reaction of a hydroxy group with an acylating agent; an amine group CH.NH$_2$, CH.NHR or CH.NR$_2$ may be prepared from a ketone or aldehyde by reductive amination); or an amide-CH.NHC(O)R or CH.N(C(O)R)$_2$ may be formed by acylation of an amine). A group X-Q-W—which is a cyano group may be reduced to an amine group.

A compound of the general formula (II) in which X represents a polymer may be prepared by reacting a compound of the general formula

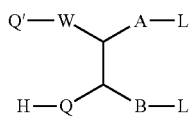
(VI)

in which Q', W, A, B and L have the meanings given above, with a polymer of the general formula

X—V (VII)

in which X represents a polymer; Q' and V being groups selected such that the compounds of (VI) and (VII) will react together to give the desired compound of the formula (II). Alternatively, a compound of the formula

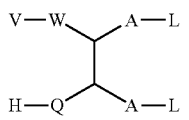
(VIII)

may be reacted with a polymer of the general formula

X-Q' (IX)

A compound of the general formula (III) may be prepared by base mediated elimination of one leaving group L from a compound of the general formula (II).

Compounds of the general formula I may include an imaging agent, for example a radio nucleotide, to enable tracking of the compound in vivo. Suitably the radio nucleotide or imaging agent I may be bound through the group W, to give, for example, compounds of the type

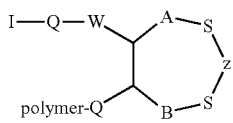

which may for example be prepared from reagents of the type

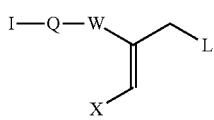 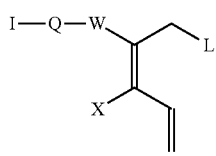

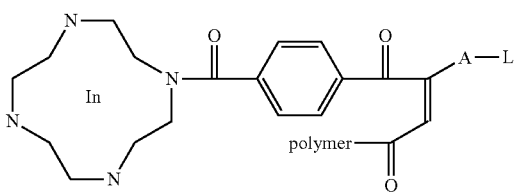

for example

The compounds of the general formula I have a number of applications. They may for example be used for direct clinical application to a patient, and accordingly, the present invention further provides a pharmaceutical composition comprising a compound of the general formula I together with a pharmaceutically acceptable carrier. The invention further provides a compound of the general formula I for use as a medicament, and a method of treating a patient which comprises administering a pharmaceutically-effective amount of a compound of the formula I or a pharmaceutical composition according to the invention to the patient. Any desired pharmaceutical effect, for example trauma treatment, enzyme replacement, toxin removal, anti-inflammatory, anti-infective, immunomodulatory, vaccination or anti-cancer, may be obtained by suitable choice of biological molecule.

The compounds of the general formula I may also be used in non-clinical applications. For example, many physiologically active compounds such as enzymes are able to catalyse reactions in organic solvents, and compounds of the general formula I may be used in such applications. Further, compounds of the general formula I may be used as diagnostic tools.

The following gives some specific biological molecules which may have utility in the present invention, depending upon the desired application. Enzymes include carbohydrate-specific enzymes, proteolytic enzymes and the like. Enzymes of interest, for both industrial (organic based reactions) and biological applications in general and therapeutic applications in particular include the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin osidase, glucose oxidase, glucuronidase, galactosidase, glucocerbrosidase, glucuronidase, glutaminase The biologically active molecules used in compounds of the general formula I of the present invention include for example factor 8, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, colony stimulating factors, hemoglobin, cytokines, antibodies, chorionicgonadotropin, follicle-stimulating hormone, thyroid stimulating hormone and tissue plasminogen activator.

Certain of the above proteins such as the interleukins, interferons and colony stimulating factors also exist in non-glycosilated form, usually the result of preparation by recombinant protein techniques. The non-glycosilated versions may be used in the present invention.

For example, for Interferons, the invention permits the preparation of conjugates in which the biological activity is retained compared with non-conjugated Interferons. This most surprising result is not possible using known conjugation techniques.

Other proteins of interest are allergen proteins disclosed by Dreborg et al Crit. Rev. Therap. Drug Carrier Syst. (1990) δ 315 365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosilated interleukins, interferons and colony stimulating factors are of interest, as are immunoglobulins such as IgG, IgE, IgM, IgA, IgD and fragments thereof.

Of particular interest are antibodies and antibody fragments which are used in clinical medicine for diagnostic and therapeutic purposes. The antibody may used alone or may be covalently conjugated ("loaded") with another atom or molecule such as a radioisotope or a cytotoxic/antiinfective drug. Epitopes may be used for vaccination to produce an immunogenic polymer-protein conjugate.

A key feature of the process of the invention is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred and bis-alkylation results from sequential and interactive Michael and retro-Michael reactions as described in J. Am. Chem. Soc. 1979, 101, 3098-3110 and J. Am. Chem. Soc. 1988, 110, 5211-5212.). The electron withdrawing group and the leaving group are optimally selected so bis-alkylation can occur by sequential Michael and retro-Michael reactions.

It is also possible to prepare cross-functional alkylating agents with additional multiple bonds conjugated to the double bond or between the leaving group and the electron withdrawing group as described in J. Am. Chem. Soc. 1988, 110, 5211-5212.

Since the cross-functionalised bis-alkylating reagents of the type mentioned above undergo alkylation that is controlled by Michael-retro Michael equilibria and since it is possible to partially reduce a number from one to a greater than one disulfide bonds in a protein in a controlled fashion significantly retaining tertiary structure, it is then possible to have bis-alkylation occur across the two sulfhydrals from cysteines of a given disulfide bond. Such a sequence of reactions results in the reannealling of the disulfide bridge with the bis-alkylating reagent.

The thiol ether bonds formed upon conjugation to give a compound of the formula I are, in general, hydrolytically stable in aqueous solution. The reagents themselves are also hydrolytically stable. In this context, a compound is regarded as being hydrolytically stable if it does not undergo substantial degradation at physiological pH and temperature up to 45° C. Degradation of less than 50% under these conditions over an eight hour period is considered insubstantial.

It will be appreciated that this invention allows the production of polymer reagents that possess cross-functionalised bis-alkylating functionality at either the termini or on pendent chains along the main chain of a polymer.

Some examples of novel conjugates according to the invention include the following:

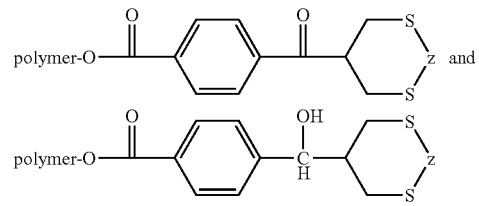

Some examples of novel reagents according to the invention include the following:

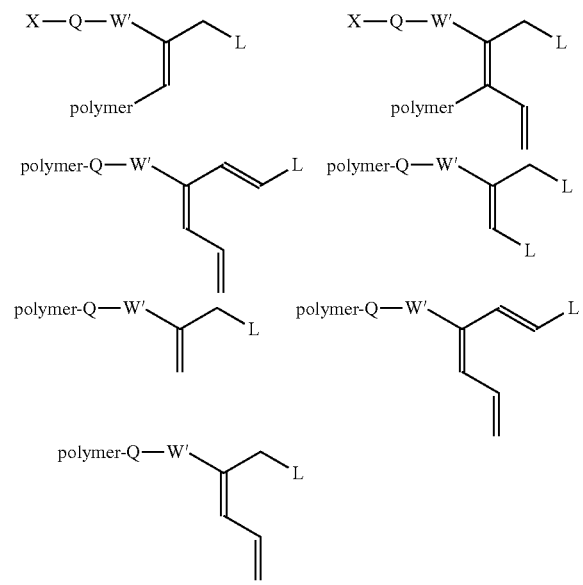

The following Examples illustrate the invention. FIGS. 1 to 5 show the results obtained from Example 7.

Example 1

Synthesis of Polymer Conjugating Reagent p-Nitro-3-piperidinopropriophenone hydrochloride: $C_{14}H_{19}ClN_2O_3$ To a single-neck 250 ml round-bottom flask was added p-nitroacetophenone (16.5 g), paraformaldehyde (4.5 g), piperidine hydrochloride (12.1 g), absolute ethanol (100 mL) and a magnetic stir bar. To the stirred heterogeneous mixture was added hydrochloric acid (37 wt % in water, 1 mL) and the solution was heated to reflux under nitrogen. After a 1-2 h period more paraformaldehyde (3.0 g) was added. The solution was allowed to reflux for approximately 18 h during which time further paraformaldehyde was added (3.0 g). After allowing the reaction solution to cool a crystalline solid settled that would not dissolve upon further refluxing. The solid was isolated by filtration and recrystallised using very hot methanol to afford large yellow crystals (10.9 g). $^1$H NMR (DMSO-d$_6$) δ 1.34-1.50 (m, 1H), 1.64-1.79 (m, 2H), 1.79-1.94 (m, 4H), 2.89-3.05 (m, 2H), 3.41 (q, 2H), 3.51-3.54 (m, 2H), 3.82 (t, 2H), 8.26 (s, 1H), 8.29 (s, 1H), 8.41 (s, 1H), 8.44 (s, 1H).

3-(2-Hydroxyethylthiol)-p-nitropropiophenone

A stirred solution of p-nitro-3-piperidinopropiophenone hydrochloride (30 g, 0.1 mol) and mercaptoethanol (9.5 g 0.12 mol) in 95% ethanol (200 ml) was slowly heated until homogeneous. Piperidine (1.0 ml) was added and the reaction mixture heated to reflux for 2 h. After cooling the majority of the solvent was rotoevaporated and ethyl acetate (200 ml) added and the solid filtered. The ethyl acetate solution was extracted sequentially with 10% aqueous HCl, 5% NaHCO$_3$ and brine, and then dried over Na$_2$SO$_4$, and then the ethyl acetate was evaporated to an oil that crystallised to give 23.2 g of the desired product that was recrystallised in ethyl acetate-ethyl ether.

2,2-Bis(p-tolylthiolmethyl)-p-nitroacetophenone: $C_{24}H_{23}NO_3S_2$

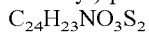

To a 100 ml single-neck round-bottom flask was added p-nitro-3-piperidinopropiophenone hydrochloride (10.0 g), 4-methylbenzenethiol (8.2 g), formaldehyde (37% w/w aq. solution, 10 ml, excess), methanol (40 ml) and a magnetic stir bar. The stirred heterogeneous mixture was heated until a yellow homogeneous solution formed (a couple of minutes at 50-60° C.). Five drops of piperidine were then added and the reaction solution heated to reflux. Within 15 min the reaction became heterogeneous due to the presence of some white/yellow solid and after 2 h this solid became a strong orange in colour. The refluxing was stopped after this time and the reaction was allowed to cool overnight to room temperature. The reaction mixture was then heated under reflux again with additional formaldehyde (37% w/w aq. solution, 10 ml, excess). After refluxing for approximately 30 min an orange oil was visible and no solid. The oil would settle to the bottom of the flask when the stirring was stopped. After a further 7 h of refluxing, the mixture was allowed to cool overnight, which resulted in the settled oil crystallising. The crystalline solid was isolated and purified by recrystallisation from very hot methanol with several drops of acetone added to afford yellow crystals (10.0 g). $^1$H NMR (DMSO-d$_6$) δ 2.31 (s, 6H), 3.31-3.33 (m, 4H), 3.97 (quintet, 1H), 7.14 (q, 8H), 7.80 (d, 2H), 8.24 (d, 2H).

2,2-Bis(p-tolylsulfonylmethyl)-p-nitroacetophenone: $C_{24}H_{23}NO_7S_2$

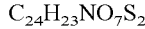

In a 250 ml round-bottom flask a suspension of 2,2-bis(p-tolylthiolmethyl)-p-nitroacetophenone (2.5 g) and Oxone (18.4 g) was stirred in a 1:1 methanol:water (100 ml) for 16 h. This afforded a white solid suspension, to which was added chloroform (100 ml) and the resulting organic phase was isolated using a separating funnel to leave a white solid suspension within the aqueous phase. Additional water was added to the aqueous phase until a homogeneous solution formed, which was then washed again with chloroform (100 ml). The organic phases were combined, washed with brine (50 mL×2), dried with magnesium sulfate and the solvent removed affording an off-white crude solid product after drying in vacuo (2.5 g). The product was recrystallised from acetone to give white crystals. $^1$H NMR (CDCl$_3$) δ 3.43-3.62 (m, 4H), 4.44 (quintet, 1H), 7.35 (d, 4H), 7.68 (d, 4H); 7.88 (d, 2H), 8.22 (d, 2H); analysis calculated for $C_{24}H_{23}NO_7S_2$ (found): C, 57.47 (57.27); H, 4.62 (4.74); N 2.79 (2.58); MS (FAB) m/z 502 ([M+1]$^+$).

2-(2-Hydroxyethylsulfonylmethyl)-p-nitro-2(Z), 4-pentadienophenone

To a flame dried round bottom flask purged with argon and fitted with a thermometer and dropping funnel was added 3-(2-hydroxyethylthiol)-p-nitropropiophenone (0.5 g, 2.0 mmol) and anhydrous tetrahydrofuran (50.0 ml). The solution was stirred and cooled by a dry ice-acetone bath, then TiCl$_4$ (0.23 ml, 2.1 mmol) was added by syringe. The ice bath was removed and the solution allowed to warm to ambient temperature, then the solution was cooled to −40° C. and diisopropylethyl amine (1.1 ml) was added by syringe. The cooling bath was removed and the reaction mixture allowed to warm to −15 to 0° C. turning a red colour. The reaction mixture was then warmed to 25° C. over a 3-5 minute period and a solution of acrolein (0.14 g, 2.1 mmol) in anhydrous tetrahydrofuran (20 ml) was added by dropping funnel over a 30-40 minute period. The exothermic reaction caused the temperature of the reaction mixture to increase to 30-40° C. and the solution stirred a further 20 minutes after addition of the aldehyde before addition of ethyl acetate (75 ml). Thin layer chromatography was used to confirm the disappearance of the starting 3-(2-hydroxyethylthiol)-p-nitropropiophenone and the formation of the desired 2-(2-hydroxyethylthiomethyl)-p-nitro-2(Z), 4 pentadienophenone (R$_f$~0.38-0.45). The minor product (E-isomer) could be observed at a lower R$_f$ in the range of 0.29-0.34. The ethyl acetate reaction mixture was extracted with 10% aqueous HCl and brine. The aqueous layers were combined and extracted twice with ethyl acetate and all the ethyl acetate fractions were combined and washed twice with 10% aqueous HCl, 5% aqueous NaHCO$_3$ and brine, then dried over solid Na$_2$SO$_4$. The ethyl acetate was rotoevaporated to give the crude 2-(2-hydroxyethylthiomethyl)-p-nitro-2(Z), 4 penta-dienophenone as an oil that was immediately oxidised as for the synthesis of 2,2-bis[(p-tolylsulfonylmethyl)]-p-nitroacetophenone to give 2-(2-hydroxyethylsulfonylmethyl)-p-nitro-2(Z), 4-pentadienophenone as a solid that was purified by column chromatography or recrystallised in ethyl acetate or methanol and then covalently bound to amino terminated poly(ethylene glycol) as described elsewhere in this specification.

The above sequence of reactions was conducted with many aldehydes including acealdehyde, methacrolein, ethacrolein butyraldehyde, crotonaldehyde, 2,4-pentadienyal, sorb-aldehyde, toluadehyde, cinnamaldehyde, methyl-cinnamaldehyde, chloro-cinnamaldehyde, 5-phenyl-2,4 pentadienal and 7-phenyl-2,4,6-heptatrienal. This sequence of reactions was conducted with many aryl keto derivatives including 3-(p-tolylthiomethyl)-m-nitroacetophenone, 3-(2-hydroxyethylthio)-m-nitropropriophenone, 3-(ethylthiomethyl)-m-nitropropiophenone, 3-(dimethylaminoethylthio)-m-nitropropiophenone, 3-(2-hydroxyethylthio)-3-phenylpropriophenone, 3(2-hydroxyethylthiol)-5-phenyl-4(E)-pentenophenone, 3(ethylthiomethyl-o-nitropropiophenone, 3-(ethylthio)-propiophenone, 3-(2-hydroxyethylsulfonyl)propiophenone, 2-(3-(2-hydroxyethylthio)-1-propenyl)-m-2(E)-4-pentadienophenone. This sequence of reactions was also conducted with aliphatic keto derivatives including 4-(ethylthio)-2-butanone, 4-(-p-tolylthio)-2-butanone, 4-(4-nitrophenylthio)-2-butanone, 4-(2-hydroxyethylthio)-2-butanone and methyl-3-(2-hydroxyethylthiol)-propanoate. The final products of the aforementioned reactions for the these precursors can be covalently bound to poly(ethylene glycol) as described elsewhere in this specification.

2,2-Bis[(p-tolylsulfonyl)methyl]-p-aminoacetophenone hydrochloride $C_{24}H_{26}ClNO_5S_2$ To a 100 mL round bottom flask was added 2,2-bis[(p-tolylsulfonyl)methyl]-p-nitroacetophenone (2 g), ethanol (25 mL), hydrochloric acid (37 wt. % in water, 8 mL) and a magnetic stir bar. To the resulting heterogeneous mixture was then added tin(II) chloride dihydrate and the mixture heated in an oil bath at 45° C. for 2 h. Water was then added to the homogeneous yellow solution that had formed to a point where it appeared that a precipitation may occur if more water was added. The homogenous solution was allowed to cool to room temperature resulting in a yellow compound crystallising/precipitating out, which was isolated by filtration under vacuum. The isolated product was then mixed with a heated mixture of acetone and methanol (approximately 90:10 v/v). An insoluble solid was isolated by filtration under vacuum and dried to constant mass in a vacuum oven (1.4 g). $^1$H NMR (DMSO-d$_6$) δ 2.50 (s, 6H), 3.57-3.73 (overlapping m's, 5H), 6.27 (s, 2H), 6.39 (d, 2H), 6.96 (d, 2H), 7.47 (d, 4H), 7.55 (d, 4H)

Coupling of 2,2-bis[(p-tolylsulfonyl)methyl]-p-aminoacetophenone to α-methoxy-ω-amino poly(ethylene glycol)

A one neck 100 mL round bottom flask fitted with a dropping funnel and nitrogen line was charged with triphosgene (23 mg), 2.2-bis[(p-tolylsulfonyl)methyl]-p-aminoacetophenone hydrochloride (125 mg), anhydrous toluene (2.5 mL) and a magnetic stir bar under a nitrogen atmosphere. The dropping funnel was separately charged with anhydrous triethylamine (68 μL) and anhydrous toluene (2.5 mL). An acetone/dry-ice bath was placed below the round bottom flask and the contents allowed to cool. The triethylamine solution was then added dropwise to the triphosgene solution under stirring over 5-10 min. The flask and dry-ice bath were allowed to warm to room temperature which took several hours and once at room temperature the reaction mixture was allowed to further stir for about 2 h, still under a nitrogen atmosphere. A solution of o-(2-aminoethyl)-O'-methylpoly (ethylene glycol) 2,000 (490 mg) and anhydrous triethylamine (68 μL) in anhydrous toluene was then added dropwise to the reaction mixture at room temperature. The resulting mixture was allowed to stir at room temperature overnight (approximately 20 h total). The reaction mixture was then opened to the atmosphere and filtered under gravity through a 5 mL disposable syringe with a piece of non-absorbent cotton wool to act as a filter. The homogeneous eluent was transferred to a 100 mL separating funnel and then washed twice with deionised water (30 mL and then 10 mL). The aqueous phases were combined and then washed with diethyl ether (approximately 25 mL). The aqueous phase was then freeze-dried to give an off-white solid product (160 mg). Product was also found in diethyl ether and toluene phases. $^1$H NMR (CDCl$_3$) δ 2.5 (s), 3.39 (s), 3.41-3.53 (overlapping m's), 3.53-3.76 (m), 3.82 (t), 4.17 (quintet), 7.35-7.39 (m, 1.39), 7.46 (d), 7.68 (d).

Example 2

Synthesis of Polymer Conjugating Reagent p-Carboxy-3-piperidinopropriophenone hydrochloride

To a 250 mL single-neck round-bottom flask was added p-acetyl benzoic acid (10 g) and piperidine hydrochloride (7.4 g), 100 mL of absolute ethanol and a magnetic stir bar. To the stirred heterogeneous mixture was added concentrated hydrochloric acid (1 mL) and the solution was then heated to reflux under nitrogen. Paraformaldehyde (3.7 g) was added to the flask and refluxing continued for approximately 1.5 h. A homogeneous solution formed to which was added more paraformaldehyde (3.7 g). Heating was continued for approximately 6 h during which time further paraformaldehyde was added (3.7 g). The reaction solution was allowed to cool to room temperature and left for 1 week. A white solid was isolated by filtration of the cooled reaction mixture. An attempt was made to crystallise the solid after dissolving in very hot methanol. An insoluble product (1.96 g) was isolated by filtration and a second product (0.88 g) crystallised out of the filtrate. Both products appeared identical by infra-red spectroscopy and thin layer chromatography analysis after drying in-vacuo and so were combined to be used in subsequent reactions. ATR-FT-IR 1704, 1691, 1235, 760.

4-[2,2-Bis[(p-tolylthio)methyl]acetyl]benzoic acid: $C_{25}H_{24}O_3S_2$

To a 50 mL single-neck round-bottom flask was added p-carboxy-3-piperidinopropriophenone hydrochloride (2.5 g), 4-methylbenzenethiol (2.1 g) formaldehyde (37% w/w aq. solution, 2.5 mL), ethanol (10 mL), a magnetic stir bar and piperidine (approximately ten drops). A condenser was then fitted to the flask and the reaction solution heated to reflux. Methanol (5 mL) was then added. After about 2 h, additional formaldehyde (2.5 mL) was added and the heating continued for a further 2 h. The reaction flask was then allowed to cool to room temperature whereupon the reaction solution was diluted with diethyl ether (approximately 150 mL). The resulting organic phase was then washed with water (acidified using 1N hydrochloric acid to pH 2-3; 50 mL×2), water (50 mL) and brine (75 mL) and then dried over magnesium sulfate. Filtration followed by removal of volatiles on a rotary evaporator afforded a solid residue. The solid was dissolved in a minimum volume of a mixture of predominately methanol and acetone with heating. The homogeneous solution was then placed in a freezer overnight, affording off-white crystals, which were isolated by filtration under vacuum, washed with fresh acetone and then dried to constant mass in a vacuum oven (2.5 g): $^1$H NMR (CDCl$_3$) δ 2.38 (s, 6H), 3.16-3.31 (m, 4H), 3.85 (quintet, 1H), 7.15 (d, 4H), 7.18 (d, 4H), 7.64 (d, 2H), 8.07 (d, 2H); analysis calculated for $C_{25}H_{24}O_3S_2$ (found): C, 68.78 (68.84); H, 5.54 (5.77).

4-[2,2-Bis[(p-tolylsulfonyl)methyl]acetyl]benzoic acid $C_{25}H_{24}O_7S_2$

In a 250 mL round-bottom flask a suspension of 4-[2,2-bis[(p-tolylthio)methyl]acetyl]benzoic acid (2 g) and Oxone (16.9 g) was stirred in 1:1 v/v methanol:water (100 mL) for 16 h. This afforded a white solid suspension to which was added chloroform (100 mL) and the resulting organic phase was isolated using a separating funnel to leave a white solid suspension with the aqueous phase. To the heterogenous aqueous phase was added additional water until homogenous (approximately 170 mL) and then the aqueous phase was washed with chloroform (75 mL). The organic phases were combined, washed with water (50 mL×2, acidified with a few drops of 1N hydrochloric acid) and brine (50 mL). The organic phase was dried with magnesium sulfate, filtered and the solvent removed using a rotary evaporator to give an off-white crude solid product (2.2 g). Further purification (on 1 g of product) was performed by recrystallisation from very hot ethyl acetate, acetone and hexane affording 0.6 g of product: $^1$H NMR (CDCl$_3$) δ 2.51 (s, 6H), 3.49-3.72 (m, 4H), 4.44 (quintet, 1H), 7.40 (d, 4H), 7.73-7.78 (m, 6H), 8.13 (d, 2H); analysis calculated for C$_{25}$H$_{24}$O$_7$S$_2$ (found): C, 59.98 (59.88); H, 4.83 (4.78).

Coupling of
4-[2,2-bis[(p-tolylsulfonyl)methyl]acetyl]benzoic
acid to α-methoxy-ω-amino PEG (2000 g/mol)

A one-neck 50 mL schlenk flask was charged with 4-[2,2-bis[(p-tolylsulfonyl)-methyl]acetyl]benzoic acid (100 mg) and a magnetic stir bar. The flask was sealed and a strong vacuum applied for approximately 15 min. An argon atmosphere was introduced into the flask and thionyl chloride (1 mL) added by syringe with stirring. The resulting mixture was heated at 50° C. for 2 h. Volatile liquids were then removed in vacuum to afford a yellow foam. An argon atmosphere was again introduced to the flask and anhydrous dichloromethane (5 mL) was added by syringe to afford a homogeneous solution. Volatile liquids were then removed again in vacuum. The solvent addition/removal process was repeated until a white residue remained. Anhydrous dichloromethane (5 mL) was again added to the schlenk flask to form a homogeneous solution. Separately in a 25 mL round bottom flask fitted with a septum and with a magnetic stir bar, O-(2-aminoethyl)-O'-methylpoly(ethylene glycol) (2,000 g/mol) (0.2 g), and anhydrous triethylamine (30 μL) were dissolved in anhydrous dichloromethane (5 mL) under an argon atmosphere. The reaction solution with bis[(p-tolylsulfonyl)-methyl]acetyl]benzoic acid was injected into the flask containing the poly(ethylene glycol) solution in a dropwise fashion, immediately resulting in the evolution of a white gas. The resulting solution was allowed to stir overnight at room temperature whereupon additional triethylamine (28 μL, was added). After a further 1 h, the reaction solution was added dropwise through a glass pipette into rapidly stirred diethyl ether. To achieve precipitation it was necessary to add hexane to the diethyl ether solution and place the flask in an ice bath. The precipitant obtained was isolated by centrifugation and dried in a vacuum oven to constant weight affording an off-white solid product (230 mg). Further purification was achieved by precipitation by first dissolving the product in dichloromethane and adding to a chilled stirred diethyl ether solution. $^1$H NMR (CDCl$_3$) δ 2.51 (s), 3.40 (s), 3.60-3.75 (m), 3.84 (t), 4.36 (quintet), 7.39 (d), 7.68 (d), 7.71 (d), 7.85 (d)

Coupling of
4-[2,2-bis[(p-tolylsulfonyl)methyl]acetyl]benzoic
acid to α-methoxy-ω-amino PEG (20,000 g/mol)

A one-neck 50 mL Schlenk flask was charged with 4-[2,2-bis[(p-tolylsulfonyl)-methyl]acetyl]benzoic acid (100 mg) and a magnetic stir bar. The flask was sealed and a strong vacuum applied for approximately 15 min. An argon atmosphere was introduced into the flask and thionyl chloride (1 mL) added by syringe with stirring. The resulting mixture was heated at 50° C. for 2 h. After allowing the flask to cool to room temperature, volatile liquids were removed in vacuum to afford a yellow foam. An argon atmosphere was again introduced to the flask and anhydrous dichloromethane (5 mL) was added by syringe to afford a homogeneous solution. Volatile liquids were then removed again in vacuum. The solvent addition-removal process was repeated until a white residue remained. Finally, anhydrous dichloromethane (5 mL) was added to the flask under argon to form a homogeneous solution.

In a separate 50 mL Schlenk flask, O-(2-aminoethyl)-O'-methylpoly(ethylene glycol) (20,000 g/mol) (0.5 g) was dissolved in 4 mL of anhydrous toluene in an argon atmosphere and then the solution was evaporated to dryness in vacuum. The white residue afforded was kept in vacuum for 3 h and then dissolved in anhydrous dichloromethane (5 mL) in an argon atmosphere.

To the poly(ethylene glycol) solution, which was stirred and cooled in an ice-water bath, was slowly added the reaction solution of bis[(p-tolylsulfonyl)-methyl]acetyl]benzoic acid drop-wise. After complete addition 40 μL of dried triethylamine was slowly added to the resulting solution dropwise. When the triethylamine had been added the resulting solution was allowed to stir overnight and warm to room temperature.

The reaction solution was then filtered through a 0.45 μm filter and volatile liquids removed from the eluent to afford a slightly yellow/orange residue that was redissolved in warm acetone (10 mL). The flask containing the resulting homogeneous-solution was placed in an ice-water bath and under stirring a precipitation occurred. The white precipitate was isolated on a no. 3 sintered glass funnel and washed with chilled fresh acetone (approximately 30 mL). The isolated solid was allowed to dry in vacuum to afford 0.4 g of white solid. $^1$H NMR (CDCl$_3$) δ 2.42 (s), 3.31 (s), 3.40-3.75 (m), 4.27 (m), 7.30 (d), 7.59 (d), 7.63 (d), 7.75 (d)

The α-methoxy-ω-4-[2,2-bis[(p-tolylsulfonyl)-methyl]acetyl]benzamide poly(ethylene glycol) conjugating reagent (20,000 g/mol) (0.4 g) was dissolved in 10 mL of an argon purged mixture of acetonitrile:water (24:1 v/v, 2 mg hydroquinone) and the solution filtered through a 0.45 μm PP filter. The eluent was placed under argon in a round-bottom flask and triethylamine (50 μL) was added under stirring. The flask was then placed in a 30° C. oil bath for 20 h with stirring after which time the flask was cooled to room temperature and the volatile liquids removed in vacuum. The residue obtained was dissolved in warm acetone (10 mL) and once homogeneous the solution was placed in an ice-water bath whereupon precipitation occurred while the solution stirred. The white precipitate was isolated on a no. 3 sintered glass funnel and washed with chilled fresh acetone (approximately 30 mL). The isolated solid was allowed to dry under vacuum to afford 0.3 g of white solid. $^1$H NMR (CDCl$_3$) δ 2.35 (s), 3.31 (s), 3.39-3.78 (m), 4.28 (s), 5.84 (s), 6.22 (s), 7.26 (d), 7.65 (d), 7.72 (d), 7.81 (d)

Example 3

Reaction of 4-methylbenzenethiol and α-methoxy-ω-4-[2,2-bis[(p-tolylsulfonyl)methyl]acetyl]benzamide poly(ethylene glycol)

The polymer conjugating reagent, α-methoxy-ω-4-[2,2-bis[(p-tolylsulfonyl)methyl]acetyl]benzamide poly(ethylene glycol) (2000 g/mol) (30 mg, 12.1 μmol, 1 eq.) and 4-methylbenzenethiol (3 mg, 24.2 mmol, 2 eq.) were dissolved in deuterated chloroform (approximately 0.75 mL). To the homogeneous solution was then added triethylamine (1.7 μL, 12.1 μmol, 1 eq.). The reaction mixture was stirred and a H-NMR spectrum was obtained. The resulting spectrum confirmed that addition of the 4-methylbenzenethiol to the polymer conjugating reagent had occurred. A similar reaction was conducted with propane triol.

Example 4

Polymer Conjugation to Ribonuclease A

To Ribonuclease A (30 mg) in a 15 mL centrifuge tube was added 3 mL of an 8M aqueous urea solution, followed by 2-mercaptoethanol (60 μL). The pH of the resulting solution was adjusted to pH 8.5 using a 10% aqueous solution of methylamine. The reaction solution was then bubbled with nitrogen for approximately 30 min. Still purging with nitrogen the tube was heated at 37° C. for 5 h. The reaction mixture was then cooled in an ice-salt water bath and 10 mL of an argon purged chilled solution of 1N HCl:absolute:ethanol (1:39 v/v) was added to the reaction solution. A precipitation occurred and the precipitate was isolated by centrifugation and then washed three times with further 10 mL portions of the HCl:absolute ethanol mixture and twice with nitrogen purged chilled diethyl ether (2×10 mL). After each washing the precipitate was isolated by centrifugation. The washed precipitate was then dissolved in nitrogen purged de-ionised water and freeze-dried to afford a dry solid. Partial reduction of Ribonuclease A was confirmed and quantitated using Ellman's Test, which gave 5.9 free thiols per protein molecule.

In an eppendorf, the partially reduced Ribonuclease A (10.9 mg) was dissolved in argon purged pH 8 ammonia solution (500 μL). In a separate eppendorf, the polymer conjugating reagent, α-methoxy-ω-4-[2,2-bis[(p-tolylsulfonyl)-methyl]acetyl]benzamide derived from poly(ethylene)glycol (2000 g/mol) (5 mg) was also dissolved in ammonia solution (250 μL) and the resulting solution added to the Ribonuclease A solution. The PEG eppendorf was washed with 250 μL of fresh ammonia solution and this was also added to the main reaction eppendorf. The reaction eppendorf was then closed under argon and heated at 37° C. for approximately 24 h and then allowed to cool to room temperature. The cooled reaction solution was then analysed by sodium dodecyl sulfate-polyacrylamide gel electrophoresis (SDS-PAGE). The SDS-PAGE experiment was consistent with reaction of pegylated 4-[2,2-bis[(p-tolylsulfonyl)methyl]acetyl]-benzoic acid with Ribonuclease A.

Example 5

Polymer Conjugation to Mouse IgG antibody Fab fragment

To 240 μL of a 0.4 mg/mL solution of mouse IgG antibody Fab fragment (Abcam Cat. No. AB6668) in an argon purged 0.02 M sodium phosphate pH 6 buffer containing 0.15 M sodium chloride and 0.005 M EDTA was added 4 μL of an argon purged aqueous solution of 1 mM selenocystamine dihydrochloride, followed by 12 μL of an argon purged aqueous solution of tris(2-carboxyethyl) phosphine hydrochloride (TCEP) at room temperature. The resulting solution was immediately vortexed for several seconds and then allowed to stand at room temperature for 6 min. Two 5 μL samples of the solution containing reduced Fab fragment were removed for future analysis and the remaining solution was then allowed to stand in an ice-water bath for 4 min. An ice-water bath chilled solution of α-methoxy-ω-4-[2,2-bis[(p-tolylsulfonyl) methyl]acetyl]benzamide derived from poly(ethylene glycol) (20,000 g/mol) (1.6 μL, 50 mg/ml, argon purged 0.02 M sodium phosphate pH 6 buffer containing 0.15 M sodium chloride, 0.005 M EDTA and 0.23 mM hydroquinone) was immediately added to the Fab solution; the solution vortexed for several seconds and then placed back into the ice-water bath. A further 1.6 μL of the conjugation reagent solution was added in an analogous manner every two minutes until 6.4 μL had been added in total. After complete addition the reaction solution was placed in a refrigerator (<5° C.) for 2 h. A sample of the reaction solution was then removed for analysis by SDS PAGE.

The reaction mixture was analysed by SEC-HPLC (100 μl injection, superpose 12-24 ml column, Amersham biosciences; eluent: 20 mM Na Phosphate, 0.15 M NaCl pH 7.0; isocratic elution for 100 min at a flow of 0.25 ml/min; UV detection, 210 nm) displaying the Fab-poly(ethylene glycol) conjugate that was not present in the identical control reaction mixture. Fractions isolated from SEC-HPLC chromatography were analysed by SDS PAGE and the mono poly(ethylene glycol) conjugate was observed.

Example 6

Polymer Conjugation to Asparaginase

A 100 μl sample of a 5 mg/ml solution of asparaginase at pH 6.5 (Sigma) was diluted with 900 μl of 20 mM phosphate buffer (pH 6 and also containing 0.15 M NaCl and 5 mM EDTA). DL-dithioreitol (DTT, 15.4 mg) was then added and the resulting solution allowed to stand at room temperature. After allowing to stand for 2 h the solution was purified on a PD-10 column (Sephadex®G-25M, Pharmacia Biotech) that had been equilibrated with 20 mM phosphate buffer (pH 6 and also containing 0.15 M NaCl and 5 mM EDTA). The column was eluted with 1 ml portions of fresh buffer. Two fractions containing reduced protein were identified using UV spectroscopy at 280 nm. These fractions were concentrated using centrifugal filter devices (MWCO 3,000; Microcon) to a volume of approximately 270 μl and then diluted to 1 ml with fresh pH 6 phosphate buffer (additionally containing 0.23 mM hydroquinone). Two 5 μl samples were removed for later analysis by SDS PAGE. Separately, a 50 mg/ml solution of the conjugating reagent solution of α-methoxy-ω-4-[2,2-bis[(p-tolylsulfonyl)methyl]acetyl]benzamide derived from poly(ethylene glycol) (20,000 g/mol) was made up in the same phosphate buffer and placed in an ice-water bath along with the protein solution for 5 min. To the protein solution was then added 58 μl of the conjugation reagent solution and after several seconds of vortexing, the reaction solution was placed in a refrigerator (<5° C.). A control reaction was also performed under the same conditions and scale but using non-reduced asparaginase. Successful poly(ethylene glycol) conjugation to asparaginase was confirmed by SDS PAGE (4-12% Bis-Tris Gel with colloidal blue staining) performed with samples taken from the reaction solution after 2 h. No conjugation band was observed by SDS PAGE for a sample taken from a control reaction where the asparaginase was not allowed to react with DTT.

Example 7

Polymer Conjugation to Interferon

A solution of 100 μl interferon α-2b (Shantha Biotechnics) (1 mg/ml) diluted with 150 μl of a buffer solution (sodium phosphate 0.02 M; NaCl 0.15 M; EDTA 0.005 M; pH 6.0 in argon purged deionised water) was partially reduced by the addition of selenocystamine (1 mM in argon purged deionised water, 2 equivalents) and TCEP (1 mM in argon purged deionised water, 5 equivalents). The protein solution was cooled to 4° C. The conjugation reagent α-methoxy-ω-4-[2,2-bis[(p-tolylsulfonyl)methyl]acetyl]benzamide derived from poly(ethylene glycol)(20,000 g/mol) was dissolved in the buffer solution (50 mg/ml), cooled to 4° C. and 16 μl added to the protein solution. The reaction mixture was vortexed and incubated at 4° C. for 2 h. The non-ionic components of the reaction mixture were removed by cation exchange chromatography (Hitrap SP FF 1 ml column, Amersham biosciences) using two buffers: (A) 25 mM Na Acetate pH 4.0 and (B) 25 mM Na Acetate+0.7 M NaCl pH 4.0. The column was washed (1 ml/min) with buffer A (5.0 ml), then buffer B (5.0 ml) and then equilibrated with 10 ml of buffer A (10 ml). The conjugate was loaded on the column (200 µl) followed by buffer A (500 µl) and a loading fraction (0.5 ml) was collected. The column was washed with 5 ml of buffer A and fractions were collected. The sample was eluted from the column with buffer B (10 ml) and fractions were collected. Spectroscopy (UV, 280 nm) was used to determine the fractions that contained protein and these fractions were then purified into separate fractions by size exclusion chromatography (100 µl injections, superose 12-24 ml column, Amersham biosciences; eluent: 20 mM Na Phosphate, 0.15 M NaCl pH 7.0; isocratic elution for 100 min at a flow of 0.25 ml/min; UV detection, 210 nm). These purification conditions provided base line resolution for the separation of the poly(ethylene glycol) interferon conjugate from native interferon. The conjugation reaction and purification of the poly (ethylene glycol) conjugate were confirmed by SDS-PAGE; 12% Bis-Tris gel (SilverQuest Silver Staining; Colloidal Blue Staining and perchloric acid 0.1 M/BaCl$_2$ 5% and I$_2$ 0.1 M staining). No conjugation was observed when a solution of 40 µl of interferon (1 mg/ml) in 60 µl of sodium phosphate 0.02 M, NaC$_1$-0.15 M, EDTA 0.005 M, pH 6.0 in argon purged water was mixed with the conjugation reagent α-methoxy-ω-4-[2,2-bis[(p-tolylsulfonyl)methyl]acetyl]benzamide derived from poly(ethylene glycol) (20,000 g/mol) was dissolved in the buffer solution (50 mg/ml), cooled to 4° C. and 16 µl added to the protein solution. This reaction mixture was vortexed and incubated at 4° C. for 2 h.

Figure 2:
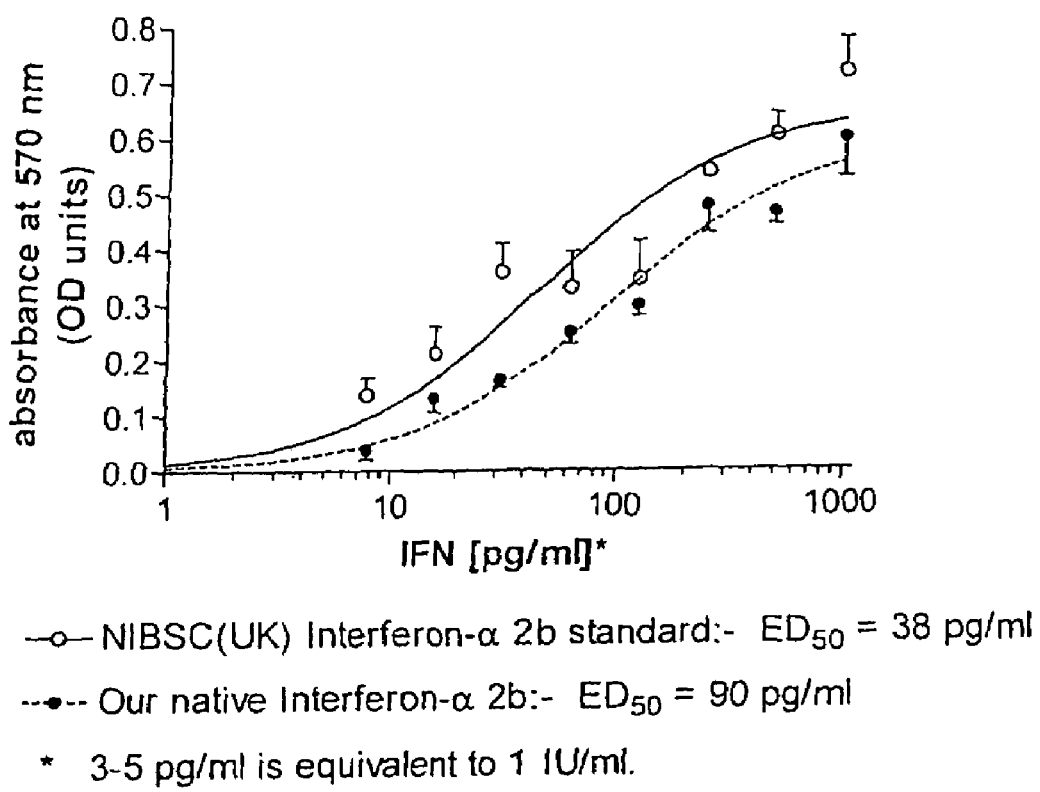
FIG. 2 shows a graph of absorbance vs. IFN [pg/ml] obtained for NIBSC (UK) interferon-α 2b (open symbols) and native interferon-α 2b (closed symbols).
Figure 3:
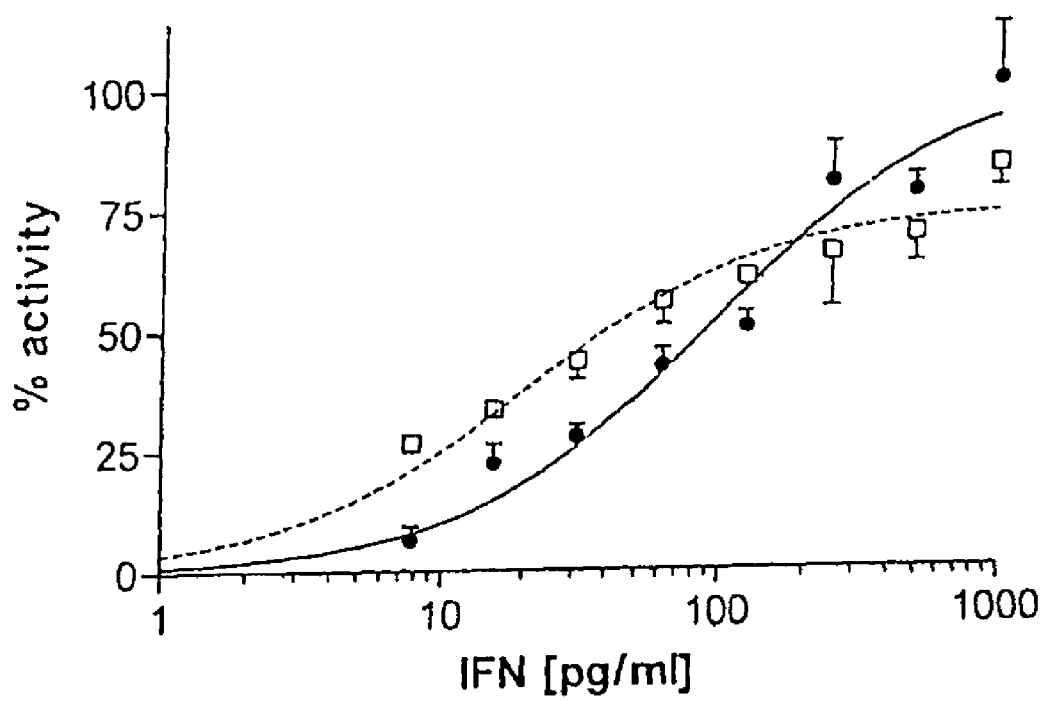
FIG. 3 shows a graph of biological activity vs. IFN [pg/ml] obtained for chemically treated native interferon-α 2b that was not pegylated (open symbols) and native interferon-α 2b (closed symbols).
Figure 4:
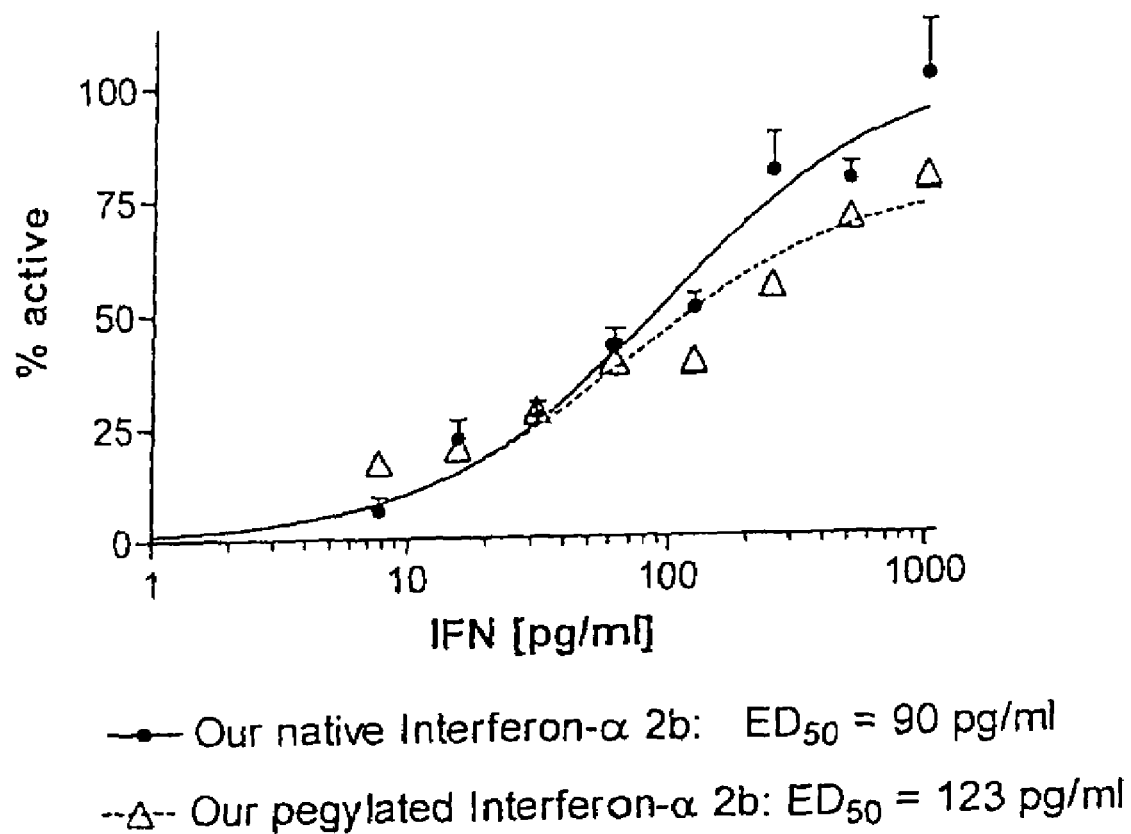
FIG. 4 shows a graph of biological activity vs. IFN [pg/ml] obtained for pegylated interferon-α 2b (open symbols) and native interferon-α 2b used for conjugation (closed symbols).

The concentration of each purified fraction of the poly (ethylene glycol) interferon conjugate was determined by enzyme immuno assay. The same assay was utilised to determine the concentration of the native interferon that was conjugated and an international standard NIBSC (UK) sample of interferon. The reproducible and accurate standard curve obtained for all forms of the aforementioned interferon is shown in FIG. 1. A549 (human lung fibroblast) cells were plated at 15,000 cells/well in 96-well flat-bottom tissue culture plates. Interferon from the NIBSC (UK), the native interferon that was conjugated and the poly(ethylene glycol) interferon conjugate were then separately added to the cells in triplicate and the plate incubated at 37° C. (5% CO$_2$) for 24 h. On the next day, a working solution of EMCV (encephalomyocarditis virus) was prepared in DMEM/2% FCS from stock virus stored at −80° C. The media containing the interferon or the poly(ethylene glycol) interferon conjugate was removed and replaced with media containing EMCV. The tissue culture plate was then incubated for 1 h at 37° C. after which the virus was removed. One hundred microlitres of DMEM/10% FCS media was added and the plate incubated for 16-24 h at 27° C. From 16 h onwards, the plate was read regularly to ascertain when cell death was starting. The media was then aspirated and the cells washed with 100 µl of phosphate buffer solution. This was followed by the addition of 50 µl of methyl violet solution [i.e., methyl violet (4% formaldehyde, 0.05% methyl violet 2B (Sigma-Aldrich)] for 30 min at room temperature. The plate was then washed with 100 µl of water and dried in air. Spectrophotometric absorbance was determined at 570 nm using a plate reader. FIG. 2 confirms that the interferon used for the conjugation had equivalent activity of the international standard NIBSC (UK) interferon. FIG. 3 confirms that native interferon used for conjugation maintained equivalent biological activity after being subjected to all the chemical and purification processes except for exposure with the poly(ethylene glycol) conjugation reagent. FIG. 4 confirms that the native interferon used for conjugation and the purified poly(ethylene glycol) interferon conjugate maintained equivalent biological activity.

Induction of 2'5'-oligoadenylate synthetase (2'5'-OAS) and protein kinase R (PRKR) mRNA by interferon-α 2b was determined. The purified poly (ethylene glycol) interferon conjugate and a sample of the native interferon-α 2b were evaluated. Two million MOLT 4 cells/well were incubated in 24 well tissue culture plates with 5000 pg of each interferon sample as measured using an enzyme immunoassay for 24 h at 37°. The total RNA was extracted (RNA II Isolation kit, Macheray-Nagel) and 200 ng subjected to reverse transcription in a final volume of 20 µL (Sigma, AMV reverse transcription kit). Samples were diluted 1 in 4 in water and 2 µL of each sample amplified in a 20 µL real-time PCR quantitation mix (Sigma SybrGreen ReadyMix). The primers used were:—

| | |
|---|---|
| 2'5'-OAS forward (SEQ ID NO: 1) | GGC TAT AAA CCT AAC CCC CAA ATC |
| 2'5'-OAS reverse (SEQ ID NO: 2) | AGC TTC CCA AGC TTC TTC TTA CAA |
| PRKR forward (SEQ ID NO: 3) | ACT CTT TAG TGA CCA GCA CAC TCG |
| PRKR reverse (SEQ ID NO: 4) | TTT AAA ATC CAT GCC AAA CCT CTT |

For 2',5'-OAS amplification, enzyme activation at 94° C. for 5 min was followed by 48 cycles of denaturation at 94° C. for 5 sec, annealing at 60° C. for 2 sec and extension at 72° C. for 8 sec. For PRKR amplification, samples were activated at 94° C. for 5 min and underwent 48 cycles of denaturation at 94° C. for 5 sec, annealing at 59° C. for 2 sec and extension at 72° C. for 8 sec. A melting curve analysis of the products was performed at the end of the amplifications. Quantitation of induced mRNA levels was done relative to the control untreated cells using the following formula:—

$$\text{Relative increase} = 2^{-(Ct\ sample - Ct\ control)}$$

where Ct is the threshold cross-over value.

Figure 5A:
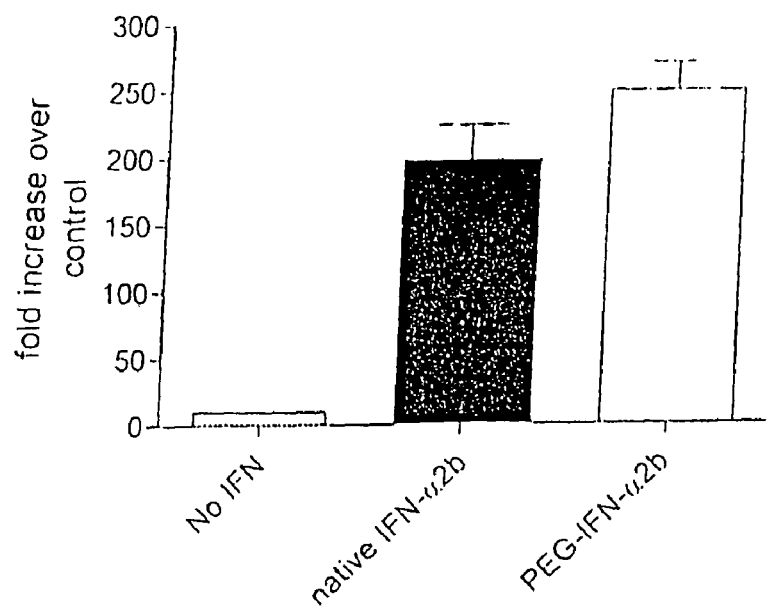
FIG. 5A shows real-time quantitative RT-PCR analysis of the interferon-inducible 2'5'-oligoadenylate synthetase (2'5'-OAS) gene.
Figure 5B:
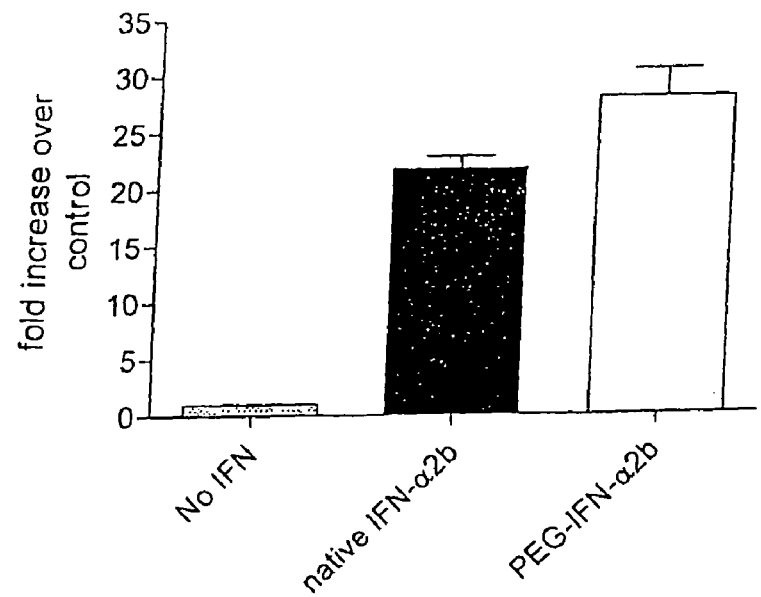
FIG. 5B shows real-time quantitative RT-PCR analysis of the interferon-inducible protein kinase R(PRKR) gene.

FIG. 5, in which FIG. 5(a) shows the real-time quantitative RT-PCR (two-step) analysis of interferon-inducible 2'5'-Oligoadenylate Synthetase (2'5'-OAS) gene, and FIG. 5(b) shows the real-time quantitative RT-PCR (two-step) analysis of interferon-inducible Protein Kinase R (PRKR) gene. The results confirm that the poly(ethylene glycol) interferon-α2b conjugate stimulated 2'5'-oligoadenylate synthetase (2'5'-OAS and protein kinase R (PRKR) mRNA synthesis to levels that were similar to native unpegylated interferon-α 2b.

The invention claimed is:

1. A process for the preparation of a protein-polymer conjugate of formula I,

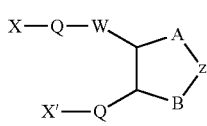

(I)

wherein
one of X and X' is a polymer and the other is a hydrogen atom;
Q is a linking group;
W is selected from the group consisting of a keto group, an ester group, a sulphone group, a reduced keto group, a reduced ester group, and a reduced sulphone group;
and if X represents a polymer, X' and W together with the interjacent atoms may form a ring;
A is a $C_{1-5}$ alkylene or alkenylene chain;
B is a bond or a $C_{1-4}$ alkylene or alkenylene chain; and
Z is a single protein linked to A and B via two thiol groups generated by the reduction of a disulfide bridge in the protein;
said method comprising the steps of:
(a) reducing a disulfide bridge in the protein; and
(b) reacting the reduced protein with either (i) a compound of formula II

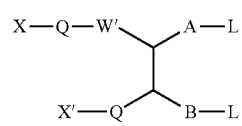

(II)

wherein X, X', Q, A and B are defined as in formula I;
W' is selected from the group consisting of a keto group, an ester group, and a sulphone group, and if X represents a polymer, X' and W' together with the interjacent atoms may form a ring;
and
L is independently a leaving group; or (ii) a compound of formula III

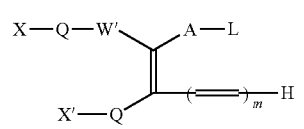

(III)

wherein X, X', Q and A are defined as in formula I,
W' is selected from the group consisting of a keto group, an ester group, and a sulphone group, and if X represents a polymer, X' and W' together with the interjacent atoms may form a ring;
L is a leaving group; and m is an integer from 1 to 4.

2. The process according to claim 1, in which each leaving group L is independently selected from the group consisting of SR, —SO$_2$R, —OSO$_2$R, —N$^+$R$_3$, —N$^+$HR$_2$, —N$^+$H$_2$R, halogen, and —OØ, in which R represents an alkyl or aryl group and Ø represents a substituted aryl group containing at least one electron withdrawing substituent.

3. A compound of the general formula II

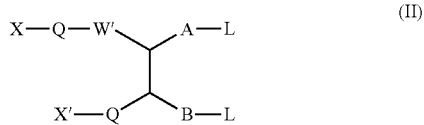

wherein one of X and X' is a polymer and the other is a hydrogen atom;
Q is a linking group;
W' is selected from the group consisting of a keto group, an ester group, and a sulphone group, and if X represents a polymer, X' and W' together with the interjacent atoms may form a ring;
A is a C$_{1-5}$ alkylene or alkenylene chain;
B is a bond or a C$_{1-4}$ alkylene or alkenylene chain; and
L is independently a leaving group.

4. A compound of the general formula III

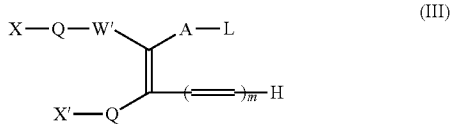

wherein one of X and X' is a polymer and the other is a hydrogen atom;
Q is a linking group;
W' is selected from the group consisting of a keto group, an ester group, and a sulphone group; and if X represents a polymer, X' and W' together with the interjacent atoms may form a ring;
A is a C$_{1-5}$ alkylene or alkenylene chain;
L is a leaving group;
and m is an integer from 1 to 4.

5. A polymer conjugating reagent comprising a compound of claim 3 or 4 in an aqueous reaction medium.

6. The process according to claim 1 further comprising reducing W' to produce a protein-polymer conjugate of formula I, wherein W is selected from the group consisting of a reduced keto group, a reduced ester group, and a reduced sulphone group.

7. The process according to claim 1, wherein polymer X or X' is a homo- or copolymer selected from the group consisting of polyalkylene glycols, polyvinylpyrrolidones, polyacrylates, polymethacrylates, polyoxazolines, polyvinylalcohols, polyacrylamides, polymethacrylamides, HPMA copolymers, polyesters, polyacetals, poly(ortho ester)s, polycarbonates, poly(imino carbonate)s, polyamides, copolymers of divinylether-maleic anhydride and styrene-maleic anhydride, polysaccharides, and polyglutamic acids.

8. The process according to claim 1, wherein polymer X or X' is a polyethylene glycol.

9. The process according to claim 1, wherein linking group Q is independently selected from the group consisting of a direct bond, an alkylene group, and an optionally-substituted aryl or heteroaryl group, any of which may be terminated or interrupted by one or more oxygen atoms, sulphur atoms, keto groups, —O—CO— groups and/or —CO—O— groups, or —NR groups in which R represents an alkyl or aryl group.

10. The process according to claim 1, which is carried out in an aqueous medium.

11. The compound of claim 3, wherein each L is independently selected from the group consisting of SR, —SO$_2$R, —OSO$_2$R, —N$^+$R$_3$, —N$^+$HR$_2$, —N$^+$N$_2$R, halogen, and —OØ, in which R represents an alkyl or aryl group and Ø represents a substituted aryl group containing at least one electron withdrawing substituent.

12. The compound of claim 3, wherein Q is independently selected from the group consisting of a direct bond, an alkylene group, and an optionally-substituted aryl or heteroaryl group, any of which may be terminated or interrupted by one or more oxygen atoms, sulphur atoms, keto groups, —O—CO— groups and/or —CO—O— groups, or —NR groups in which R represents an alkyl or aryl group.

13. The compound of claim 3, wherein polymer X or X' is a polyethylene glycol.

14. The compound of claim 4, wherein L is selected from the group consisting of SR, —SO$_2$R, —OSO$_2$R, —N$^+$R$_3$, —N$^+$HR$_2$, —N$^+$H$_2$R, halogen, and —OØ, in which R represents an alkyl or aryl group and Ø represents a substituted aryl group containing at least one electron withdrawing substituent.

15. The compound of claim 4, wherein Q is independently selected from the group consisting of a direct bond, an alkylene group, and an optionally-substituted aryl or heteroaryl group, any of which may be terminated or interrupted by one or more oxygen atoms, sulphur atoms, keto groups, —O—CO— groups and/or —CO—O— groups, or —NR groups in which R represents an alkyl or aryl group.

16. The compound of claim 4, wherein polymer X or X' is a polyethylene glycol.

* * * * *

UNITED STATES PATENT AND TRADEMARK OFFICE
CERTIFICATE OF CORRECTION

| | |
|---|---|
| PATENT NO. | : 7,939,630 B2 |
| APPLICATION NO. | : 12/458931 |
| DATED | : May 10, 2011 |
| INVENTOR(S) | : Brocchini et al. |

Page 1 of 1

It is certified that error appears in the above-identified patent and that said Letters Patent is hereby corrected as shown below:

Title Page, Item (63) Change "January 11, 2006" to --July 12, 2004--.

In the Specification

Column 1, line 10, change "January 11, 2006" to --July 12, 2004--.

Signed and Sealed this
Twenty-ninth Day of March, 2016

Michelle K. Lee
*Director of the United States Patent and Trademark Office*

SEQUENCE LISTING

<160> NUMBER OF SEQ ID NOS: 4

<210> SEQ ID NO 1
<211> LENGTH: 24
<212> TYPE: DNA

-continued

```
<213> ORGANISM: Artificial Sequence
<220> FEATURE:
<223> OTHER INFORMATION: synthetic PCR primer

<400> SEQUENCE: 1
ggctataaac ctaaccccca aatc                                         24

<210> SEQ ID NO 2
<211> LENGTH: 24
<212> TYPE: DNA
<213> ORGANISM: Artificial Sequence
<220> FEATURE:
<223> OTHER INFORMATION: synthetic PCR primer

<400> SEQUENCE: 2
agcttcccaa gcttcttctt acaa                                         24

<210> SEQ ID NO 3
<211> LENGTH: 24
<212> TYPE: DNA
<213> ORGANISM: Artificial Sequence
<220> FEATURE:
<223> OTHER INFORMATION: synthetic PCR primer

<400> SEQUENCE: 3
actctttagt gaccagcaca ctcg                                         24

<210> SEQ ID NO 4
<211> LENGTH: 24
<212> TYPE: DNA
<213> ORGANISM: Artificial Sequence
<220> FEATURE:
<223> OTHER INFORMATION: synthetic PCR primer

<400> SEQUENCE: 4
tttaaaatcc atgccaaacc tctt                                         24
```